United States Patent [19]

Berge

[11] Patent Number: 4,863,946
[45] Date of Patent: Sep. 5, 1989

[54] 2-[2H-(1,3-DIHYDROISOINDOLE)AL-KYLENE]-4,5-DIHYDROIMIDAZOLES AND PHARMACEUTICAL COMPOSITIONS THEREOF

[75] Inventor: John M. Berge, Surrey, England

[73] Assignee: Beecham Group plc, Middlesex, England

[21] Appl. No.: 936,162

[22] Filed: Dec. 1, 1986

[30] Foreign Application Priority Data

Nov. 30, 1985 [GB] United Kingdom ............... 8529546

[51] Int. Cl.⁴ ................. A61K 31/415; C07D 403/06
[52] U.S. Cl. ................... 514/397; 514/374; 540/593; 544/333; 446/148; 548/238; 548/336
[58] Field of Search ............... 548/336, 238; 514/397, 514/374

[56] References Cited

U.S. PATENT DOCUMENTS 3,661,927 5/1972 Zivkovic ............................ 544/336

FOREIGN PATENT DOCUMENTS 0072954 1/1971 European Pat. Off. .
2219418 11/1972 Fed. Rep. of Germany .
1670143 10/1973 Fed. Rep. of Germany .
1360044 3/1964 France .
526562 9/1972 Switzerland .
2021100 11/1979 United Kingdom .

Primary Examiner—Glennon H. Hollrah
Assistant Examiner—James H. Turnipseed
Attorney, Agent, or Firm—Hopgood, Calimafde, Kalil, Blaustein & Judlowe

[57] ABSTRACT

A compound of formula (I):

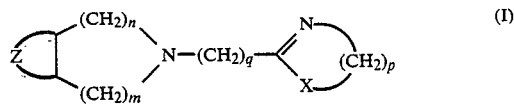

or a pharmaceutically acceptable salt, ester or amide thereof, wherein:

Z represents a residue of a substituted or unsubstituted aryl group,

X represents O or $NR^o$ wherein $R^o$ represents a hydrogen atom, a substituted or unsubstituted alkyl group, a substituted or unsubstituted aryl group, an alkanoyl group substituted or unsubstituted in the alkyl moiety, or an arylalkyl moiety substituted or unsubstituted in the aryl moiety.

n represents an integer 1 or 2,
m represents an integer 1 or 2,
p represents an integer 2 or 3, and
q represents an integer in the range of from 1 to 12;
pharmaceutical compositions containing such compounds and the use of such compounds and compositions in medicine.

14 Claims, No Drawings

2-[2H-(1,3-DIHYDROISOINDOLE)ALKYLENE]-4,5-DIHYDROIMIDAZOLES AND PHARMACEUTICAL COMPOSITIONS THEREOF

This invention relates to a class of novel heterocyclic compounds having activity as anti-hyperglycaemic agents and/or anti-hypertensive agents, to a process or preparing such compounds, to pharmaceutical compositions containing such compounds and the use of such compounds and compositions in medicine.

British Patent Application, Publication No. 2021100A and European Patent Specification, Publication Number 0,072,954 disclose certain heterocyclic compounds which are described as having long lasting anti-hypertensive activity.

A novel class of heterocyclic compounds has now been discovered which are structurally distinct from the GB 2021100A and EPO, 072,954 compounds. The novel heterocyclic compounds surprisingly show good $\alpha_2$-adrenocepter antagonist activity and they are therefore of potential use in the treatment and/or prophylaxis of hyperglycaemia and/or glaucoma and/or the treatment of hypertension and/or depression and/or for inhibiting blood platelet aggregation.

Accordingly, the present invention provides a compound of formula (I):

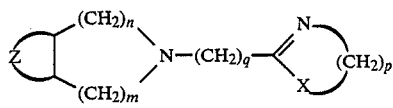

or a pharmaceutically acceptable salt, ester or amide thereof, wherein:

Z represents a residue of a substituted or unsubstituted aryl group,

X represents O or NR$^o$ wherein R$^o$ represents a hydrogen atom, a substituted or unsubstituted alkyl group, a substituted or unsubstituted aryl group, an alkanoyl group substituted or unsubstituted in the alkyl moiety, or an arylalkyl moiety substituted or unsubstituted in the aryl moiety, n represents an integer 1 or 2, m represents an integer 1 or 2, p represents an integer 2 or 3, and q represents an integer in the range of from 1 to 12.

Suitably Z represents the residue of an aryl group comprising single or fused 5- or 6- membered rings, such as a phenyl, naphthyl, anthracyl or phenanthrenyl group.

Favourably, Z represents the residue of a phenyl or naphthyl group.

Preferably, Z represents the residue of a phenyl group.

Suitable optional substitutents for any aryl group include up to 5 preferably up to 3, groups selected from halogen, alkyl, alkenyl, alkynyl, phenyl, haloalkyl, hydroxy, alkoxy, arylalkyloxy, amino, mono and di- alkyl- amino, aminoalkyl, mono- and di-alkylaminoalkyl, nitro, carboxy, carboxyalkyl, alkoxycarbonyl, alkoxycarbonylalkyl or alkylcarbonyl.

Suitable optional substituents for any alkyl group include those mentioned above in relation to the aryl group.

Suitably, X represents NR$^o$.

Suitably, R$^o$ represents hydrogen, alkyl or alkanoyl.

Suitably, q represents an integer in the range of from 1 to 6.

In one aspect the present invention provides a compound falling within the scope of formula (I) of formula (II):

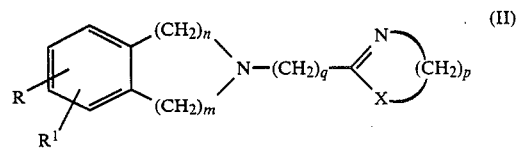

or a pharmaceutically acceptable salt, ester or amide thereof, wherein R and R$^1$ each independently represents hydrogen, alkyl, amino, mono- or di- alkyl amino, hydroxy, alkoxy, carboxy, or a halogen atom, and X, R$^o$, m, n, p and q are as defined in relation to formula (I).

Suitably, R and R$^1$ each independently represents hydrogen, alkyl, halogen or alkoxy.

Preferably R and R$^1$ each independently represents hydrogen or halogen.

When used herein the term "halogen" refers to fluorine, chlorine, bromine and iodine; preferably chlorine.

When used herein the term "in-vivo" hydrolysable ester" relates to a pharmaceutically acceptable ester which readily breaks down in the human or non-human animal body to leave for example in relation to an in-vivo hydrolysable ester of a carboxy group the free carboxy group or a salt thereof or for example in relation to an in-vivo hydrolysable ester of an hydroxy group, the free hydroxy group, or a salt thereof.

When used herein the term "alkyl", "alkenyl", "alkynyl" or "alkoxy" relates to groups having straight or branched chains containing up to 12 carbon atoms.

Suitable alkyl groups are $C_{1-12}$ alkyl groups especially $C_{1-6}$ alkyl groups e.g. methyl, ethyl, n-propyl, iso-propyl, n-butyl, isobutyl or tert-butyl groups.

Suitable alkenyl groups are $C_{2-12}$ groups especially $C_{2-6}$ alkenyl groups.

Suitable alkynyl groups are $C_{2-12}$ alkynyl groups especially $C_{2-6}$ alkynyl groups.

Preferably X represents NH. Preferably, n represents the integer 1. Preferably, m represents the integer 1. Preferably, p represents the integer 2. Preferably, q represents the integer 1.

In a favoured aspect of the present invention there is provided a group of compounds, falling within the scope of formula (I), of formula (III);

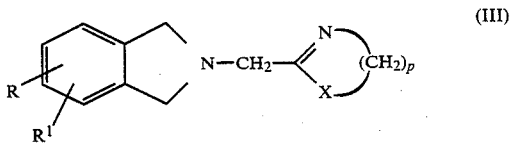

or a pharmaceutically acceptable salt, ester or amide thereof; wherein X and p are as defined in relation to formula (I) and R and R$^1$ are as defined in relation to formula (II).

In a further favoured aspect the present invention provides a group of compounds, falling within the scope of formula (I), of formula (IV):

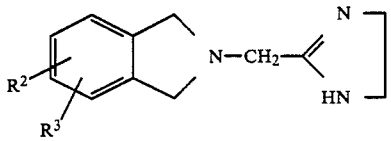

or a pharmaceutically acceptable salt, ester or amide thereof, wherein $R^2$ and $R^3$ each independently represents hydrogen, $C_{1-6}$ alkyl or halogen.

Favourably, $R^2$ represents hydrogen.

Favourably, $R^2$ represents halogen, preferably chlorine.

Favourably $R^2$ represents $C_{1-6}$ alkyl.

In a preferred aspect the present invention provides a compound selected from the group consisting of:
2-[2H-(1,3-dihydroisoindole)methyl]-4,5-dihydroimidazole;
2-[2H-(4-chloro-1,3-dihydroisoindole)methyl]-4,5-dihydroimidazole;
2-[2H-(5-chloro-1,3-dihydroisoindole)methyl]-4,5-dihydroimidazole;
2-[(1,2,3,4-tetrahydroisoquinoline)methyl]-4,5-dihydroimidazole;
2-[2H-(5-fluoro-1,3-dihydroisoindole)methyl]-4,5-dihydroimidazole;
2-[2H-(5-methoxy-1,3-dihydroisoindole)methyl)-4,5-dihydroimidazole dihydrochloride; and
2-[2H-(5-methyl-1,3-dihydroisoindole)methyl]-4,5-dihydroimidazole; or a pharmaceutically acceptable salt, ester or amide thereof.

Suitable pharmaceutically acceptable salts of the compound of formula (I) include acid addition salts, salts of carboxy groups and salts of hydroxy groups.

Suitable pharmaceutically acceptable acid addition salts of compound (I) include pharmaceutically acceptable inorganic salts such as the sulphate, nitrate, phosphate, borate, hydrochloride and hydrobromide and pharmaceutically acceptable organic acid addition salts such as acetate, tartrate, maleate, citrate, succinate, benzoate, ascorbate, methane-sulphonate, α-keto glutarate, α-glycerophosphate, and glucose-1-phosphate. Preferably the acid addition salt is a hemisuccinate, hydrochloride, α-ketoglutarate, α-glycerophosphate or glucose-1-phosphate, in particular the hydrochloride salt.

Suitable pharmaceutically acceptable salts of carboxy groups include metal salts, such as for example aluminium, alkali metal salts such as sodium or potassium, alkaline earth metal salts such as calcium or magnesium and ammonium or substituted ammonium salts, for example those with lower alkylamines such as triethylamine, hydroxy-lower alkylamines such as 2-hydroxyethylamine, bis-(2-hydroxyethyl)-amine or tri-(2-hydroxyethyl) -amine, cycloalkylamines such as bicyclohexylamine, or with procaine, dibenzylpiperidine, N-benzyl-β-phenethylamine, dehydroabietylamine, N,N'-bisdehydroabietylamine, glucamine, N-methylglucamine or bases of the pyridine type such as pyridine, collidine or quinoline.

Suitable pharmaceutically acceptable salts of hydroxyl groups include metal salts, especially alkali metal salts such as sodium and potassium salts.

Suitable pharmaceutically acceptable esters of compounds of formula (I) include esters of carboxy groups and hydroxy groups.

Favoured pharmaceutically acceptable esters are in-vivo hydrolysable esters of carboxy groups and hydroxy groups.

Examples of suitable in-vivo hydrolysable esters of carboxyl groups include those which break down readily in the human body to leave the parent acid or its salt. Suitable ester groups of this type include those of part formula (i), (ii) and (iii):

wherein $R^a$ is hydrogen, methyl, or phenyl, $R^b$ is $C_{1-6}$ alkyl, $C_{1-6}$ alkoxy or phenyl; or $R^a$ and $R^b$ together form a 1,2-phenylene group optionally substituted by one or two methoxy groups;

$R^c$ represents $C_{1-6}$ alkylene optionally substituted with a methyl or ethyl group—

$R^d$ and $R^e$ independently represent $C_{1-6}$ alkyl;

$R^f$ represents $C_{1-6}$ alkyl.

Examples of suitable in vivo hydrolysable ester group include for example acyloxyalkyl groups such as acetoxymethyl, pivaloyloxy-methyl, α-acetoxyethyl and α-pivaloyloxyethyl groups; alkoxycarbonyloxyalkyl groups, such as ethoxycarbonyl-oxymethyl and α-ethoxycarbonyloxyethyl; dialkylamino-alkyl especially di-loweralkylamino alkyl groups such as dimethylaminomethyl, dimethylaminoethyl, diethylaminomethyl or diethylaminoethyl and lactone groups such as phthalidyl and dimethoxyphthalidyl.

Suitable in-vivo hydrolysable esters of hydroxyl groups include those provided by $C_{1-6}$ alkyl carboxylic acids.

Suitable pharmaceutically acceptable amides include amides of formula —CO. $NR^s R^t$ wherein $R^s$ and $R^t$ each independently represent hydrogen or $C_{1-6}$ alkyl; or $R^s$ and $R^t$ together with the nitrogen to which they are attached represent a saturated 5- or 6- membered ring.

The present invention also provides a process for the preparation of a compound of formula (I), or a pharmaceutically acceptable salt, ester or amide thereof, which process comprises cyclising a compound of formula (V):

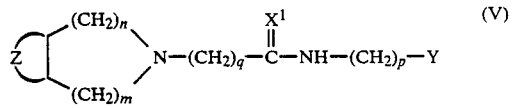

wherein Z, n, m, p and q are as defined in relation to formula (I), $X^1$ represents O or NH and Y represents $OR^g$ wherein $R^g$ is hydrogen or a hydroxyl protecting group, or —$NHR^h$ wherein $R$ represents hydrogen or a nitrogen protecting group; providing that when $X^1$ is O then Y is ORG and when $X^1$ is NH then Y is $NHR^h$;

and thereafter is required carrying out one or more of the following optional steps:

(i) removing any protecting groups;

(ii) converting a compound of formula (I) into a further compound of formula (I);

(iii) converting a compound of formula (I) into a pharmaceutically acceptable salt, ester or amide thereof;

A compound of formula (V) may be prepared by reacting a compound of formula (VI):

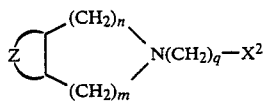

(VI)

wherein Z, n, m and q are as defined in relation to formula (I) and $X^2$ represents CN, or $CO_2R^6$ wherein $R^6$ represents hydrogen or an alkyl group, with a compound of formula (VII):

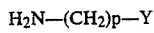

(VII)

wherein p is defined in relation to formula represents $OR^g$ when $X^2$ is $-CO_2R^6$ and Y represents $-NR^h$ when $X^2$ is CN.

A compound of formula (VI) may be prepared by reacting a compound of formula (VIII):

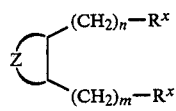

(VIII)

wherein Z, n and m are as defined in relation to formula (I) and $R^x$ represents a leaving group, with a compound of formula (IX):

(IX)

or an acid addition salt thereof, preferably a hydrochloride, wherein q and $X^2$ are as defined in relation to formula (VI).

The compounds of formula (VIII) are either known compounds or may be prepared using methods analogous to those used for known compounds: for example the compound of formula (VIII) wherein Z represents a 3-chlorophenyl group, n and m each represent the integer 1 and Rx represents a bromine atom, may be prepared by the following route from 3-chlorophthalic anhydride:

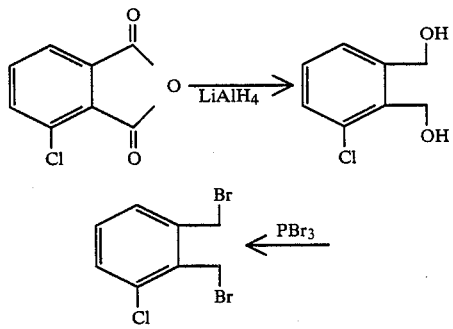

The compounds of formula (VII) and (IX) are known commercially available compounds or may be prepared by processes analogous to those used to prepare such compounds.

The cyclisation of compounds of formula (V) may be carried out under any appropriate conditions, using any suitable solvent system and temperature range, but usually at an elevated temperature.

Favourably for compounds of formula (I) wherein X represents O the cyclisation of the compound of formula (V) is carried out in the presence of a dehydrating agent, such as phosphoryl chloride. Conveniently the reaction is carried out in toluene, or any other suitable solvent, preferably at the reflux temperature of the chosen solvent.

Suitably, for the preparation of compounds of formula (I) wherein X represents $NR^o$, the compounds of formula (V) from the reaction between the appropriate compounds of formula (VI) and (VII) are not isolated they are converted in-situ to compounds of formula (I).

Favourably, for the preparation of compounds of formula (I) wherein X represents $-NR^o$; the appropriate compounds of formula (VI) and formula (VII) are reacted together at an elevated temperature, for example within the range 80° C. to 130° C., preferably 110° C., in any suitable solvent; the reaction is preferably carried out using the appropriate compound of formula (VII) as solvent in the presence of a catalytic amount of carbon disulphide; preferably the reaction is carried out under an atmosphere of nitrogen. It will be understood that under the abovementioned conditions the compound of formula (V) initially formed undergoes cyclisation to give the compound of formula (I).

Thus in an alternative aspect the present invention provides a process for the preparation of a compound of formula (I) wherein X represents $NR^o$, which process comprises reacting a compound of formula (VI) wherein $X^2$ represents CN, with a compound of formula (VII) wherein Y represents $NR^o$; and thereafter if required carrying out one or more of the following optional steps:

(i) removing any protecting groups;

(ii) converting a compound of formula (I) into a further compound of formula (I);

(iii) converting a compound of formula (I) into a pharmaceutically acceptable salt, ester or amide thereof, The reaction between compounds of formula (VIII) and (IX) is conveniently carried out in an aprotic solvent, such as dimethylformamide, preferably at a temperature of between 20° C. and 60° C.; the reaction being continued until conventional monitoring techniques indicate that the reaction is suitably complete.

Suitable hydroxyl and nitrogen protecting groups are those used conventionally in the art; for example a suitable hydroxyl protecting group is a benzyl group.

A preferred nitrogen protecting group $R^h$ is a moiety $R^o$ as defined in relation to formula (I).

A compound of formula (I) may be converted into a further compound of formula (I) by using any appropriate conventional method, for example compounds wherein $R^o$ is hydrogen may be converted to a compound wherein $R^o$ is other than hydrogen by conventional alkylation, arylation, alkanoylation or aralkylation methods. Similarly compounds of formula (I) wherein $R^o$ is other than hydrogen may be converted to compounds of formula (I) wherein $R^o$ is hydrogen by conventional dealkylation, dearylation, dealkanoylation or dearylalkylation methods.

The present invention also provides a compound of the general formula (I), or a pharmaceutically acceptable salt, ester or amide thereof, for use as an active therapeutic substance.

The present invention provides a compound of the general formula (I), or a pharmaceutically acceptable salt, ester or amide thereof, for use in the treatment of and/or prophylaxis of hyperglycaemia in human or non-human mammals.

In a further aspect the present invention also provides a compound of formula (I) or a pharmaceutically acceptable salt, ester or amide thereof, for use in the treatment and/or prophylaxis of glaucoma and/or the treatment of depression and/or for inhibiting blood platelet aggregation.

In a further aspect, the present invention provides a compound of the general formula (I), or a pharmaceutically acceptable salt, ester or amide thereof, for use in the treatment of hypertension in human or non-human mammals.

A compound of the general formula (I), or a pharmaceutically acceptable salt, ester or amide thereof, may be administered per se or, preferably, as a pharmaceutical composition also comprising a pharmaceutically acceptable carrier.

Accordingly, the present invention also provides a pharmaceutical composition comprising a compound of the general formula (I), or a pharmaceutically acceptable salt, ester or amide thereof, and a pharmaceutically acceptable carrier therefor.

As used herein the term "pharmaceutically acceptable" embraces compounds, compositions and ingredients for both human and veterinary use: for example the term "pharmaceutically acceptable salt" embraces a veterinarily acceptable salt.

The composition may, if desired, be in the form of a pack accompanied by written or printed instructions for use.

Usually the pharmaceutical compositions of the present invention will be adapted for oral administration, although compositions for administration by other routes, such as by injection, percutaneous absorption and, especially for the treatment and/or prophylaxis of glaucoma, topical application to the eye, are also envisaged.

Particularly suitable compositions for oral administration are unit dosage forms such as tablets and capsules. Other fixed unit dosage forms, such as powders presented in sachets, may also be used.

In accordance with conventional pharmaceutical practice the carrier may comprise a diluent, filler, disintegrant, wetting agent, lubricant, colourant, flavourant or other conventional adjuvant.

Typical carriers include, for example, microcrystalline cellulose, starch, sodium starch glycollate, polyvinylpyrrolidone, polyvinylpolypyrrolidone, magnesium stearate, sodium lauryl sulphate or sucrose.

Most suitably the composition will be formulated in unit dose form. Such unit dose will normally contain an amount of the active ingredient in the range of from 0.1 to 1000 mg, more usually 0.1 to 500 mg, and more especially 0.1 to 250 mg.

As indicated above in relation to the treatment and/or prophylaxis of glaucoma, a compound of formula (I), or a pharmaceutically acceptable salt, ester or amide thereof, may also be administered as a topical formulation in combination with conventional topical excipients. Such formulations will of course be suitably adapted for administration to the eye.

The topical formulations of the present invention may be presented as, for instance, eye ointments, creams or lotions or eye drops or other conventional formulations suitable for administration to the eye, and may contain appropriate conventional additives such as preservatives, solvents to assist drug penetration and emollients in ointments and creams. The formulations may also contain compatible conventional carriers, such as eye ointment, cream or lotion bases and solvents suitable for administration to the eye. Such carriers may be present as from about 20% up to about 99.5% of the formulation.

Suitable eye ointments, creams or lotions, eye drops or other conventional formulations suitable for administration to the eye are conventional formulations well known in the art, for example, as described in standard text books of pharmaceutics and cosmetics, such as Harry's Cosmeticology published by Leonard Hill Books, Remington's Pharmaceutical Sciences, and the British and U.S. Pharmacopoeias.

Suitably, the compound of formula (I) or a pharmaceutically acceptable salt, ester or amide thereof will comprise from about 0.5 to 20% by weight of the topical formulation, favourably from about 1 to 10%, for example 2 to 5%.

The present invention further provides a method for the treatment and/or prophylaxis of hyperglycaemia in a human or non-human mammal which comprises administering an effective, non-toxic, amount of a compound of the general formula (I), or a pharmaceutically acceptable salt, ester or amide thereof, to a hyperglycaemic human or non-human mammal in need thereof.

The present invention further provides a method for the treatment of hypertension in a human or non-human mammal, which comprises administering an effective, non-toxic, amount of a compound of the general formula (I), or a pharmaceutically acceptable salt, ester or amide thereof, to an hypertensive human or non-human mammal.

The invention also provides a method for the treatment and/or prophylaxis of glaucoma and/or the treatment of depression and/or inhibiting blood platelet aggregation in a human or non-human mammal, which method comprises administering an effective non-toxic amount of a compound of formula (I), or a pharmaceutically acceptable salt, ester or amide thereof, to a human or non-human animal in need thereof.

Conveniently, the active ingredient may be administered as a pharmaceutical composition hereinbefore defined and this forms a particular aspect of the present invention.

In the treatment and/or prophylaxis of hyperglycaemic humans or the treatment of hypertensive humans the compound of the general formula (I), or a pharmaceutically acceptable salt, ester or amide thereof, may be taken in doses, such as those described above, one to six times a day in a manner such that the total daily dose for a 70 kg adult will generally be in the range of from 0.1 to 6000 mg, and more usually about 1 to 1500 mg.

In the treatment and/or prophylaxis of hyperglycaemic non-human mammals, especially dogs, the active ingredient may be administered by mouth, usually once or twice a day and in an amount in the range of from about 0.025 mg/kg to 25 mg/kg, for example 0.1 mg/kg to 20 mg/kg.

In the treatment and/or prophylaxis of glaucoma (via non-topical regimes) and the treatment of depression and inhibition of platelet aggregation in human or non-human mammals, dosage regimes are as indicated above for the treatment and/or prophylaxis of hyperglycaemic human or non-human mammals.

The present invention also provides the use of a compound of formula (I), or a pharmaceutically acceptable salt, ester or amide thereof, for the manufacture of a medicament for the treatment and/or prophylaxis of hyperglycaemia and/or the treatment of hypertension.

The present invention further provides the use of a compound of formula (I) or a pharmaceutically acceptable salt, ester or amide thereof, for the manufacture of a medicament for the treatment and/or prophylaxis of glaucoma and/or the treatment of depression and/or for the inhibition of blood platelet aggregation.

No toxicological effects are indicated when a compound of formula (I), or a pharmaceutically acceptable salt, ester or amide thereof, is administered in any of the abovementioned dosage ranges.

The following Examples illustrate the invention but do not limit it in any way.

EXAMPLE 1

2-[2H-(1,3-Dihydroisoindole)methyl]-4,5-dihydroimidazole

A mixture of 3.6 g (22.8 mmole) of 2H-(1,3-dihydroisoindole)-2-acetonitrile, 1.39 g (22.8 mmole) of 1,2-diaminoethane and a catalytic amount of carbon disulphide was heated at 110° C. under nitrogen for 6 hours. The mixture was allowed to cool and solidify; 50 ml of water was added to the resultant crystalline mass and filteration gave a yellow solid. Recrystallisation from ethyl acetate afforded the title compound as a white solid, m.p. 156°–158° C. (decomp.).

$^1$H nmr $\delta$(CDCl$_3$): 7.3–7.1 (4H, m); 4.5–4.0 (1H, broad m, exchanges with D$_2$O); 3.95 (4H,s); 3.64 (4H,s); 3.53 (2H,s).

IR (KBr): 1612 cm$^{-1}$.

EXAMPLE 2

2-[2H-(4-Chloro-1,3-dihydroisoindole)methyl]-4,5-dihydroimidazole

The title compound, m.p. 157°–160°C. (ethyl acetate), was prepared from 4.2 g (21.8 mmole) of 2H-[4-chloro-1,3-dihyroisoindole)-2-acetonitrile and 1.33 g (21.8 mmole) of 1,2-diaminoethane by an analogous method to that described in Example 1.

$^1$H nmr $\delta$ (CDCl$_3$): 7.5–7.0 (3H,m); 4.5–3.9 (1H, broad m, exchanges with D$_2$O); 4.04 (4H,s); 3.64 (4H,s); 3.55 (2H,s).

IR (KBr): 1615 cm$^{-1}$.

EXAMPLE 3

2-[2H-(5-Chloro-1,3-dihydroisoindole)methyl]-4,5-dihydroimidazole

The title compound, m.p. 167°–169°C. (decomp.) (ethyl acetate), was prepared from 6.0 g (31.2 mmole) of H-[5-chloro-1,3-dihydroisoindole)-2-acetonitrile and 1.88 g(31.2 mmol) of 1,2-diaminoethane by an analogous method to that described in Example 1.

$^1$H-nmr $\delta$ (CDCl$_3$): 7.3–7.1 (3H,m); 4.9–4.7(1H,broad m, exchanges with D$_2$); 3.91(4H,s); 3.60(4H,s); 3.48(2H,s).

EXAMPLE 4

2-[(1,2,3,4-Tetrahydroisoquinoline)methyl]-4,5-dihydroimidazole

The title compound, m.p. 120°–122° C. (ethyl acetate), was prepared from 5.0 g (28.9 mmole) of [1,2,3,4-tetrahydroisoquinoline]-2-acetonitrile and 1.79 g (29.9 mmole) of 1,2-diaminoethane by an analogous method to that described in Example 1.

$^1$H-nmr $\delta$ (CDCl$_3$): 7.3–7.0 (4H,m); 5.0–4.7 (1H,broad m, exchanges with D$_2$); 3.7–3.5 (6H,m); 3.32 (2H, s); 3.0–2.7(4H,m).

EXAMPLE 5

2-[2H-(5-Fluoro-1,3-dihydroisoindole)methyl]-4,5-dihydroimidazole

The title compound, m.p. 170°–172° C. (ethyl acetate) was prepared from 1.5 g (8.52 mmole) of 2H-[5-fluoro-1,3-dihydroisoindole)-2-acetonitrile and 0.6 g (10 mmole) of 1,2-diaminoethane by an analogous method to that described in Example 1.

$^1$H-nmr $\delta$(CDCl$_3$): 7.3–6.7 (3H, m); 4.85 (1H, broad s, exchanges with D$_2$); 3.95 (4H, s); 3.62 (4H, s); 3.52 (2H, s).

EXAMPLE 6

2-[2H-(5-Methoxy-1,3-dihydroisoindole)methyl]-4,5 dihydroimidazole dihydrochloride The title compound, m.p. 241°–243° C. (ethanol), was prepared from 2.2 g (11.7 mmole) of 2H-(5-methoxy-1,3-dihydroisoindole)-2-acetonitrile and 0.78 g (13.0 mmole) of 1,2-diaminoethane by an analogous procedure to that described in Example 1. Conversion to the salt was achieved by treating a solution of the free base in ethyl acetate with excess ethereal hydrogen chloride.

$^1$H-nmr $\delta$ (DMSO): 11.0–10.7 (2H, broad s, exchanges with D$_2$); 7.28 (1H, d); 6.96 (1H, d); 6.90 (1H, dd); 4.56 (4H, d); 4.49 (2H, S); 4.6–4.4 (1H, broad, exchanges with D$_2$); 3.90 (4H, s); 3.76 (3H, s).

EXAMPLE 7

2-[2H-(5-Methyl-1,3-dihydroisoindole)methyl]-4,5-dihydroimidazole

The title compound, m.p. 153°–155° C. (ethyl acetate) was prepared from 3.5 g (20.3 mmole) of 2H-[5-methyl-1,3-dihydroisoindole)-2-acetonitrile and 1.35 g (22.5 mmole) of 1,2-diaminoethane by an analogous procedure to that described in Example 1.

$^1$H-nmr $\delta$(CDCl$_3$): 7.2–6.9 (3H, m); 5.00 (1H, s, exchanges with D$_2$O); 3.97 (4H, s); 3.62 (4H, s); 3.51 (2H, s); 2.36 (3H, s).

EXAMPLE X1

2H-(1,3-Dihydroisoindole)-2-acetonitrile

To a mixture of 40 g (0.432 mole) of aminoacetonitrile hydrochloride and 90 ml (0.659 mole) of triethylamine in 200 ml of dry dimethylformamide at 50° C. under nitrogen was added dropwise with stirring 62 g (0.235 mole) 1,2-bisbromomethylbenzene in 100 ml of dry dimethylformamide. The reaction temperature was kept below 60° C. during the addition. After stirring overnight at room temperature the mixture was poured into 600 ml of water, the organic product was extracted with 3×500 ml portions of diethyl ether. The organic layer was washed water (×1) and saturated sodium chloride solution (×1), dried and evaporated to yield the crude nitrile. Vacuum distillation afforded the title compound as a pale yellow oil, b.p. 108°-110° C./0'mm which crystallised on standing at room temperature.

$^1$H nmr $\delta$(CDCl$_3$): 7.3–7.0 (4H,m); 4.05 (4H,s); 3.72 (2H,s).

EXAMPLE X2

1,2-Bishydroxymethyl-3-chlorobenzene

To a suspension of 5 g of lithium aluminium hydride in 50 ml of dry diethyl ether was added dropwise with stirring a solution of 10 g (54.8 mmole) of 3-chlorophthalic anhydride in 120 ml of dry tetrahydrofuran. After heating under reflux for 6 hours, the mixture was cooled and treated carefully with 5 ml of water, 5 ml of 10% sodium hydroxide solution and 10 ml of water. The solution was filtered, the filtrate was dried over magnesium sulphate, filtered and evaporated to yield the title compound as a colourless waxy solid.

$^1$H nmr $\delta$(CDCl$_3$) 7.5–7.0 (3H,m); 4.79 (2H,s); 4.60 (2H,s); 4.4-3.9 (2H, broad m, exchanges with D$_2$O).

EXAMPLE X3

1,2-Bisbromomethyl-3-chlorobenzene

To a solution of 6.8 g (39.4 mmole) of 1,2-bishydroxymethyl-3-chlorobenzene in 150 ml of dry diethyl ether was added dropwise with stirring 17.5 ml (186 mmole) of phosphorous tribromide in 50 ml of diethyl ether while the temperature of the reaction was kept below 30° C. After stirring at room temperature for 18 hours the resultant solution was poured into ice/water (500 ml). The aqueous layer was saturated with sodium chloride and the organic layer separated, dried and evaporated to yield the title compound as a yellow oil, which crystallised on standing. The product was used without further purification.

$^1$H nmr $\delta$(CDCl$_3$): 7.5–6.9 (3H, complex m); 4.9–4.7 (2H,m); 4.6–4.3 (2H,m).

EXAMPLE X4

2H-(4-Chloro-1,3-dihydroisoindole)-2-acetonitrile

The title compound was prepared from 4 g (43.2 mmole) of aminoacetonitrile hydrochloride, 13 g (129 mmole) of triethylamine and 11 g (36.9 mmole) of 1,2-bisbromomethyl-3-chlorobenzene by an analogous method to that described in Example X1.

$^1$H nmr $\delta$(CDCl$_3$): 7.6–7.0 (3H, complex m); 4.4–3.4 (6H, complex m).

EXAMPLE X5

1,2-Bishydroxymethyl-4-chlorobenzene

The title compound was prepared from 25 g (124.6 mmole) of 4-chlorophthalic acid by an analogous procedure to that described in Example X2. $^1$H-nmr $\delta$ (CDCl$_3$): 7.4–7.1(3H,m); 4.57(2H,broad m, exchanges with D$_2$O); 4.50(4H,s).

EXAMPLE X6

1,2-Bisbromomethyl-4-chlorobenzene

The title compound, b.p. 120°-125°C./0.2mm, was prepared from 17 g (98.6 mmole) of 1,2-bishydroxymethyl-4-chlorobenzene and 40 ml (422 mmole) of phosphorous tribromide by an analogous procedure to that described in Example X3.

$^1$H-nmr $\delta$ (CDCl$_3$): 7.5–7.2(3H,m); 4.54(4H,s).

EXAMPLE X7

2H-(5-Chloro-1,3-dihydroisoindole)-2-acetonitrile

The title compound was prepared from 17.6 g (59 mmole) of 1,2-bisbromomethyl-4-chlorobenzene, 10 g (100 mmole) of aminoacetonitrile hydrochloride and 25 ml (183 mmole) of triethylamine by an analogous procedure to that described in Example X1.

$^1$H-nmr $\delta$ (CDC13): 7.4–7.1(3H,m); 4.07(4H,s); 3.81 (2H,s).

EXAMPLE X8

[1,2,3,4-Tetrahydroisoquinoline]-2-acetonitrile

To a mixture of 26.5 g (199 mmol) of 1,2,3,4-tetrahydroisoquinoline and 30 g(283 mmol) of sodium carbonate in 100 ml of butanone under reflux was added dropwise 11.8 ml (186 mmol) of chloroacetonitrile in 20 ml of butanone. After 1 h the mixture was cooled, filtered and solvent evaporated. Vacuum distillation, bp. 135°-138° C./0.3 mm, of the crude product gave the title compound as a yellow oil.

$^1$H-nmr $\delta$ (CDCl$_3$): 7.2–6.8 (4H,m); 3.75(2H,s); 3.56(2H,s); 3.1–2.7(4H,m).

Example X9

1,2-Bishydroxymethyl-4-fluorobenzene

The title compound was prepared from 7.3 g (34.4 mmole) of dimethyl 4-fluorophthalate by an analogous procedure to that described in Example X2.

$^1$H-nmr $\delta$ (CDCl$_3$): 7.5–6.8 (3H, m); 4.66 (4H, s); 4.5–4.2 (2H, broad m, exchanges with D$_2$O).

EXAMPLE X10

1,2-Bisbromomethyl-4-fluorobenzene.

The title compound was prepared from 4.4 g (28.2 mmole) of 1,2-bishydroxymethyl-4-fluoro benzene and 15 ml (158 mmole) of phosphorus tribromide by an analogous procedure to that described in Example X3.

$^1$H-nmr $\delta$ (CDCl$_3$): 7.4–6.8 (3H, m); 4.55 (4H, s).

EXAMPLE X11

2H-(5-Fluoro-1,3-dihydroisoindole)-2-acetonitrile

The title compound was prepared from 3.6 g (12.8 mmole) of 1,2-bisbromomethyl-4-fluorobenzene, 2.0 g (20.4 mmole) of aminoacetonitrile hydrochloride and 9.2 ml (67.4 mmole) of triethylamine by an analogous procedure to that described in Example X1.

$^1$H-nmr $\delta$ (CDCl$_3$) 7.3–6.7 (3H, m); 4.08 (4H, s); 3.11 (2H,s). EXAMPLE X12

1,2-Bishydroxymethyl-4-methoxybenzene

The title compound was prepared from 7.7 g (34.4 mmole) $^1$H-nmr $\delta$ (CDCl$_3$): 7.3–7.0 (1H, m); 6.9–6.7 (2H, m); 4.47 (4H, s); 4.2–3.9 (2H, broad m, exchanges with D$_2$O); 3.72 (3H, s).

EXAMPLE X13

1,2-Bischloromethyl-4-methoxybenzene

The title compound was prepared from 4.5 g (26.8 mmole) of 1,2-bishydroxymethyl-4-methoxybenzene and 25ml (286 mmole) of thionyl chloride by an analogous procedure to that described in Example X3.

$^1$H-nmr $\delta$ (CDCl$_3$): 7.4–7.1 (1H, m); 7.0–6.8 (2H, m); 4.63 (4H, s); 3.71 (3H, s).

EXAMPLE X14

2H-(5-Methoxy-1,3-dihydroisoindole)-2-acetonitrile

The title compound was prepared from 5.2 g (25.4 mmole) of 1,2-bischloromethyl-4-methoxybenzene, 3.0 g (30.5 mmole) of aminoacetonitrile hydrochloride and 12 ml (85.5 mmole) of triethylamine by an analogous procedure to that described in Example X1.

$^1$H-nmr $\delta$ (CDCl$_3$): 7.3–7.0 (1H, m); 7.0–6.7 (2H, m); 4.04 (4H, s); 3.9–3.8 (5H, m).

Example X15

1,2-Bishydroxymethyl-4-methylbenzene

The title compound was prepared from 25 g (154 mmole) of 4-methylphthalic anhydride by an analogous procedure to that described in Example X2.

$^1$H-nmr $\delta$ (CDC13): 7.2–6.9 (3H,m); 4.45 (4H,s); 4.2–3.8 (2H, broad m, exchanges with D$_2$O) 2.30 (3H,s).

EXAMPLE X16

1,2-Bischloromethyl-4-methylbenzene

The title compound was prepared from 15 g (99 mmole) of 1,2-bishydroxymethyl-4-methylbenzene and 20 ml (230 mmole) of thionyl chloride by an analogous procedure to that described in Example X3.

$^1$H-nmr $\delta$ (CDCl$_3$): 7.4–7.0 (3H,m); 4.55 (4H,s); 2.28 (3H,s).

EXAMPLE X17

2H-(5-Methyl-1,3-dihydroisoindole)-2-acetonitrile

The title compound was prepared from 16 g (84 mmole) of 1,2-bischloromethyl-4-methylbenzene, 10 g (100 mmole) of aminoacetonitrile hydrochloride and 44 ml (322 mmole) of triethylamine by an analogous method to that described in Example X1.

$^1$H-nmr $\delta$ (CDCl$_3$):
7.2–6.9 (3H,m); 4.00 (4H,s); 3.79 (2H,s); 2.30 (3H,s).

DEMONSTRATION OF EFFECTIVENESS OF COMPOUNDS

(A) Reversal of Adrenaline-Exacerbated Glucose Intolerance in Mice

CFLP female mice of about 25 g were fasted for 24 hours prior to receiving water (10 ml/kg) or compounds by oral gavage. Thirty minutes later, glucose (1 g/kg) and adrenaline (300 μg/kg) were injected subcutaneously. Blood samples for glucose analysis were taken serially from the tail of each mouse at 0, 30, 60, 90 and 120 minutes after dosing glucose and the results are expressed below as the percentage reduction in the area under the blood glucose curve; the compound treated groups being compared to the water dosed control group. Six mice were used in each treatment group.

| Example No: | Dose (μmol/kg) | % Reduction in area under Blood Glucose Curve |
| --- | --- | --- |
| 1 | 10 | 40 |
| 2 | 10 | 24 |
| 3 | 20 | 44 |

(A) α2-Adrenoceptor Binding

Human platelet membranes were incubated with [$^3$H] Rauwolscine (0.5–1.0 nM) for 30 minutes at 30° C. with varying concentrates of the drug (0.1–10,000 nM). The binding assay was stopped by filtering and rinsing on GF/B glass fibre filters. Binding Affinity (Ki) was calculated using the Ching Prussoff equation.

| Example No: | Binding Affinity. Ki (nM) |
| --- | --- |
| 1 | 5 |
| 2 | 7 |
| 3 | 13 |
| 4 | 20 |
| 5 | 164 |
| 6 | 89 |
| 7 | 22 |

I claim:

1. A compound of formula (I):

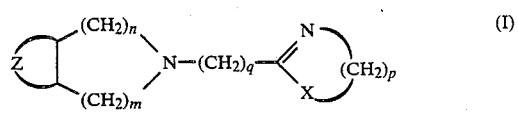

or a pharmaceutically acceptable salt, ester or amide thereof, within:

Z represents a residue of a substituted or unsubstituted aryl group, said aryl group being a phenyl or naphthyl group, X represents 0 or NR$^O$ wherein R$^O$ represents a hydrogen atom, a substituted or unsubstituted alkyl group, a substituted or unsubstituted aryl group, an alkanoyl group substituted or unsubstituted in the alkyl moiety, or an arylalkyl moiety substituted or unsubstituted in the aryl moiety, n represents an integer 1, m represents an integer 1, p represents an integer 2, and q represents an integer in the range of from 1 to 12;

and wherein the substituents for any aryl group or alkyl group includes up to five groups selected from halogen, alkyl, alkenyl, alkynyl, phenyl, haloalkyl, hydroxy, alkoxy, arylalkyloxy, amino, mono- an di- alkylamino, aminoalkyl, mono- an di-alkylaminoalkyl, nitro, carboxy, carboxyalkyl, alkoxycarbonyl, alkoxycarbonylaklyl or alkylcarbonyl.

2. A compound according to claim 1 of formula (II):

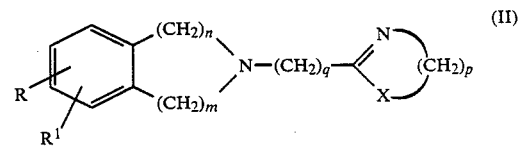

or a pharmaceutically acceptable salt, ester or amide thereof, wherein R and R$^1$ each independently represents hydrogen, alkyl, amino, mono- or di- alkyl amino, hydroxy, alkoxy, carboxy, or a halogen atom, and X, R$^o$, m, n, p and q are as defined in relation to formula (I).

3. A compound according to claim 1, wherein X represents NH.

4. A compound according to claim 1, wherein q represents the integer 1.

5. A compound according to claim 1, of formula (III):

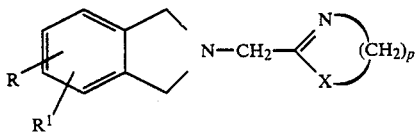

or a pharmaceutically acceptable salt, ester or amide thereof; wherein X and p are as defined in relation to formula (I) and R and R¹ each independently represents hydrogen, alkyl, amino, mono- or di- alkyl amino, hydroxy, alkoxy, carboxy, or a halogen atom.

6. A compound according to claim 1, of formula (IV):

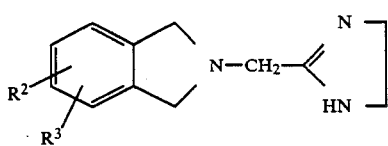

or a pharmaceutically acceptable salt, ester or amide thereof, wherein $R^2$ and $R^3$ each independently represents hydrogen, $C_{1-6}$ alkyl or halogen.

7. A compound according to claim 1, selected from the list consisting of:
2-[2H-(1,3-dihydroisoindole)methyl]-4,5-dihydroimidazole;
2-[2H-(4-chloro-1,3-dihydroisoindole)methyl]-4,5-dihydroimidazole;
2-[2H-(5-chloro-1,3-dihydroisoindole)methyl]-4,5-dihydroimidazole;
2-[2H-(5-fluoro-1,3-dihydroisoindole)methyl]-4,5-dihydroimidazole;
2-[2H-(5-methoxy-1,3-dihydroisoindole)methyl]-4,5-dihydroimidazole dihydrochloride; and
2-[2H-(5-methyl-1,3-dihydroisoindole)methyl]- 4,5-dihydroimidazole; or a pharmaceutically acceptable salt, ester or amide thereof.

8. 2-[2H-(1,3-Dihydroisoindole)methyl]-4,5-dihydroimidazole, or a pharmaceutically acceptable salt, ester or amide thereof.

9. 2-[2H-(4-1 -Chloro-1,3-dihydroisoindole)methyl]-4,5-dihydroimidazole, or a pharmaceutically acceptable salt, ester or amide thereof.

10. 2-[2H-(5-Chloro-1,3-dihydroisoindole)methyl]-4,5-dihydroimidazole, or a pharmaceutically acceptable salt, ester or amide thereof.

11. 2-[2H-(5-Fluoro-1,3-dihydroisoindole)methyl]-4,5-dihydroimidazole, or a pharmaceutically acceptable salt, ester or amide thereof.

12. 2-[2H-(5-Methoxy-1,3-dihydroisoindole) methyl]-4,dihydroimidazole dihydrochloride, or a pharmaceutically acceptable salt, ester or amide thereof.

13. 2-[2H-(5-Methyl-1,3-dihydroisoindole)methyl]-4,5-dihydroimidazole; or a pharmaceutically acceptable salt, ester or amide thereof.

14. A pharmaceutical composition comprising a compound of claim 1 of the formula (I), or a pharmaceutically acceptable salt, ester or amide thereof, and a pharmaceutically acceptable carrier therefor.

* * * * *